United States Patent

Hamada et al.

[11] Patent Number: 5,856,284
[45] Date of Patent: Jan. 5, 1999

[54] DETERGENT COMPOSITION INCLUDING A GLYCEROL DERIVATIVE, A POLYHYDRIC ALCOHOL, AND AN AMPHOTERIC SURFACTANT

[75] Inventors: Hirokazu Hamada, Chiba; Kiyoko Nakagaki, Tokyo; Masaki Itabashi, Kamagaya, all of Japan

[73] Assignee: Kao Corporation, Tokyo, Japan

[21] Appl. No.: 873,456

[22] Filed: Jun. 12, 1997

Related U.S. Application Data

[63] Continuation of Ser. No. 562,993, Nov. 27, 1995, Pat. No. 5,681,804, which is a continuation of Ser. No. 232,423, Apr. 21, 1994, Pat. No. 5,496,492, which is a continuation of Ser. No. 919,737, Jul. 27, 1992, abandoned.

[30] Foreign Application Priority Data

Jul. 26, 1991 [JP] Japan ..................................... 3-187531

[51] Int. Cl.$^6$ ............................. C09D 9/00; A61K 7/021
[52] U.S. Cl. .......................... 510/137; 510/422; 510/501; 510/499; 510/505; 554/213; 554/227; 514/738; 514/784; 514/786; 514/943; 424/63; 424/64; 424/59; 424/70
[58] Field of Search ..................................... 510/137, 422, 510/499, 119, 501, 502, 505; 554/213, 227; 514/938, 784, 773, 785, 786, 943, 939; 424/63, 64, 59, 70

[56] References Cited

U.S. PATENT DOCUMENTS

| | | | |
|---|---|---|---|
| 4,122,085 | 10/1978 | Douglass | 260/294.8 |
| 5,080,889 | 1/1992 | Katada et al. | 424/63 |
| 5,461,170 | 10/1995 | Miyamoto et al. | 554/213 |

*Primary Examiner*—Paul Lieberman
*Assistant Examiner*—Necholus Ogden
*Attorney, Agent, or Firm*—Oblon, Spivak, McClelland, Maier & Neustadt, P.C.

[57] ABSTRACT

A detergent composition comprising:

(A) glycerol derivative having the following Formula (I)

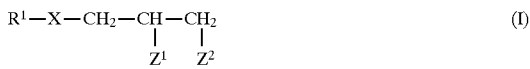

(B) a water-soluble polyhydric alcohol; and (C) at least one surfactant selected from the group consisting of an anionic surfactant, wherein component (A) and component (C) are in a ratio of from 2:1 to 1:100 by weight. When the detergent composition is used to clean skin, the skin remains moisturized after cleaning without stickiness or tackiness and without excess degreasing or dryness.

11 Claims, No Drawings

DETERGENT COMPOSITION INCLUDING A GLYCEROL DERIVATIVE, A POLYHYDRIC ALCOHOL, AND AN AMPHOTERIC SURFACTANT

This is a Continuation of application Ser. No. 08/562,993 filed on Nov. 27, 1995 now U.S. Pat. No. 5,686,804, which is a continuation of 08/232,423 filed Apr. 21, 1994, now U.S. Pat. No. 5,496,492, which is a continuation of 07/919,737 filed Jul. 27, 1992, abandoned.

BACKGROUND OF THE INVENTION

1. Field of the Invention

The present invention relates to a detergent composition which is primarily used on the skin, and more particularly to a detergent composition to gently moisturize skin without causing excess degreasing or dryness after cleaning.

2. Discussion of the Background

Conventional skin detergents are used to wash away dirt or soil caused by such substances as sebum or sweat. Unfortunately, strong skin detergents often cause excess degreasing and dryness by removing many of the skin's natural oils and moisturizers. Thus, it is highly desirable to balance the cleaning ability of the detergent with its ability to moisturize the skin and leave it feeling refreshed after cleaning, without leaving a sticky or tacky feeling.

Conventional methods of hydrating the skin after cleaning include the application of cosmetics such as a toilet water and a milky lotion comprising moisturizers. Another approach to solving the above problem has been to mix the moisturizer with the detergent. Moisturizers, including polyhydric alcohols, such as glycerol, propylene glycol, and sorbitol, have been used. However, due to the presence, in skin of high levels of lipids, such as intercellular lipid and sebum, it is difficult for these water-soluble moisturizers to permeate the corneal layer, even when blended with the detergent.

Additionally, when the detergent is removed by rinsing, the moisturizer is also removed. Furthermore, moisturizes incorporated into a detergent sometimes provide unfavorable sticky or tacky feeling.

Accordingly, a detergent composition is desired which combines cleaning effect with a sufficient moisturizing effect, without leaving the skin with an unpleasant feeling, such as stickiness or tackiness.

SUMMARY OF THE INVENTION

Accordingly, one object of the present invention is to provide a detergent composition which cleans and moisturizes the skin without leaving the skin feeling sticky or tacky.

These and other objects have been satisfied by the discovery that a detergent composition comprising a glycerol derivative, a polyhydric alcohol and a surfactant, will allow a moisturizer to readily permeate the corneal layer to cleanse and moisturize skin without causing stickiness or tackiness.

In accordance with one aspect of the present invention, there is provided a detergent composition comprising:

(A) a glycerol derivative having the following formula (I)

wherein one of $Z^1$ and $Z^2$ represents $R^2$—Y— and the other of $Z^1$ and $Z^2$ represents —OH and wherein $R^1$ and $R^2$ represent hydrocarbon groups having a total carbon atom number of 13 to 40 and X and Y represent an oxygen atom or

(B) a water-soluble polyhydric alcohol; and
(C) at least one surfactant selected from the group consisting of an anionic surfactant, an amphoteric surfactant and a nonionic surfactant, wherein component (A) and component (C) are present in a ratio of from 2:1 to 1:100 by weight.

Various other objects, features, and attendant advantages of the present invention will be more fully understood from the following detailed description.

DESCRIPTION OF THE PREFERRED EMBODIMENTS

The detergent composition of the present invention comprises:

(A) a glycerol derivative having the following formula (I)

wherein one of $Z^1$ and $Z^2$ represents $R^2$—Y— and the other of $Z^1$ and $Z^2$ represents —OH and wherein $R^1$ and $R^2$, which may be the same or different, represent hydrocarbon groups having a total carbon atom number of 13 to 40 and X and Y represent an oxygen atom or

(B) a water-soluble polyhydric alcohol; and
(C) at least one surfactant selected from the group consisting of an anionic surfactant, an amphoteric surfactant and a nonionic surfactant, wherein component (A) and component (C) are present in a weight ratio of from 2:1 to 1:100.

Components (A), (B), and (C) are present in the detergent composition of the present invention in amounts of 0.1–20%, 1–90%, and 2–60% by weight respectively.

The glycerol derivatives of component (A) are represented by formula (I):

Preferred glycerol derivatives are those which are liquid at 20° C. or higher. Further, these glycerol derivatives can be divided into two groups including dialkylglyceryl ethers and diacyl glycerols depending on whether X and Y represent oxygen atoms or

Dialkylglyceryl ethers can be used, such as 1,3-dialkylglyceryl ethers which are represented by formula (II):

wherein $R^1$ and $R^2$ are as described above.

Preferred combinations of $R^1$ and $R^2$ in formula (II) includes cases where $R^1=R^2$=octyl, $R^1$=lauryl, $R^2$=methyl; $R^1$=myristyl, $R^2$=methyl; $R^1$=stearyl, $R^2$=butyl; $R^1$=2-heptylundecyl, $R^2$=methyl; $R^1$=oleyl, $R^2$=methyl; $R^1$=oleyl, $R^2$=butyl; $R^1$=oleyl, $R^2$=octyl; $R^1$ and $R^2$=2-ethylhexyl; and $R^1$=2-ethyl-hexyl, $R^2$=octyl.

Diacyl glycerols can also be used, such as 1,2-diacyl glycerol and 1,3-diacyl glycerol. These diacyl glycerols can be obtained by separating and refining by processes such as molecular distillation, or solvent extraction of a fatty acid glycerol ester (containing not less than 60% of diester). Such a fatty acid glycerol ester may be obtained by any conventional method, such as esterification of a glycerol and a fatty acid, glycerolysis of a glycerol and a natural animal or vegetable fat/oil or a hydrogenated natural animal or vegetable fat/oil, or glycerolysis of a higher fatty acid higher alcohol ester and a glycerol. Alternatively, one may use conventional enzymatic methods utilizing lipase, instead of the above non-enzymatic methods.

Preferable diacyl esters include di-(2-ethylhexanoic acid) glycerol ester, dioctanoic acid glycerol ester, dioleic acid glycerol ester, diesters of myristic acid and methyl-branched isostearic acid represented by formula (III):

$$CH_3(CH_2)_m-\underset{\underset{CH_3}{|}}{CH}-(CH_2)_n-COOH \quad (III)$$

wherein m and n are integers of 4 to 10 and m+n=14, having a distribution centering around m=n=7, {5,7,7-trimethyl-2-(1,3,3-trimethylbutyl)-octanoic acid} myristic acid glycerol diester (two of three -OH groups of glycerol are reacted with 5,7,7-trimethyl-2-(1,3,3-trimethylbutyl)-octanoic acid and myristic acid to form two ester connections), and (2-heptylundecanoic acid) myristic acid glycerol diester.

The glycerol derivative of component (A) is present at a level of from 0.1 to 20 weight % (hereinafter referred to as %), preferably 0.5 to 10%, more preferably 0.5 to 5%, in the detergent composition.

Component (B) may include any water-soluble polyhydric alcohol, such as ethylene glycol, diethylene glycol, dipropylene glycol, propylene glycol, butylene glycol, glycerol, diglycerol, or sorbitol. Of these, propylene glycol, butylene glycol, ethylene glycol, glycerol and sorbitol are particularly preferred due to their high water-solubility. Component (B) is present at a level of from 1 to 90%, preferably 1 to 30%, more preferably 5 to 25% in the detergent composition of the present invention.

While components (A) and (B) may be mixed at any ratio and temperature which provides effective dissolution, it is preferred to mix the water-soluble polyhydric alcohol of component (B) with the glycerol derivative of component (A) in any mixing ratio at 20° C.

Component (C) is at least one surfactant chosen from the group consisting of anionic surfactants, amphoteric surfactants and nonionic surfactants. Suitable anionic surfactants include paraffin sulfonate, a-olefin sulfonate, alkylbenzene sulfonate, (polyoxyethylene) alkyl ether sulfate, (polyoxyethylene)alkyl ether carboxylate, mono- or dialkyl phosphate, acyl isothionate, N-acyl amino acid, N-acyl-N-alkyltaurin, alkylcarboxylic acid, and dermatologically acceptable salts of these compounds. Suitable salts include alkali metal salts, such as sodium or potassium, ammonium salts, and organic ammonium salts such as monoethanol ammonium, diethanol ammonium, or triethanol ammonium.

Suitable amphoteric surfactants include betainic surfactants such as imidazolium betaine, carbobetaine, sulfobetaine and the like.

Suitable nonionic surfactants include polyoxyethylene-alkyl ether, polyoxyethylenepolypropylenealkyl ether, alkyl glycosides represented by formula (IV)

$$R^3O(R^4O)_tG_u \quad (IV)$$

wherein $R^3$ represents a $C_8$–$C_{18}$ alkyl, $C_8$–$C_{18}$ alkylphenyl, $C_8$–$C_{18}$ hydroxy-alkyl or $C_8$–$C_{18}$ hydroxyalkylphenyl group, $R^4$ represents $C_2$–$C_4$ alkyl group, t is an integer of 0 to 5, G represents a group derived from a $C_5$–$C_6$ reducing sugar and u represents a number of from 1 to 3.

The amount of component (c) present varies depending on detergent types and requirements of the detergent composition and ranges from 2 to 60%, preferably 10 to 50%, preferably 10 to 40%.

Further, the weight ratio of component (A) and component (c) is 2:1 to 1:100, preferably 1:2 to 1:50, more preferably 1:5 to 1:30.

In the detergent composition of the present invention, various other conventional detergent additives may be used in addition to those listed above, as long as the particular additive does not adversely affect the function of the detergent composition. These conventional additives may include viscosity regulators, such as anionic polymers, nonionic polymers or cationic polymers, conditioners, moisturizers other than the aforementioned moisturizers, preservatives, perfumes, and pigments.

The detergent composition of the present invention can be produced using conventional methods. While the physical form of the present detergent composition is not restricted in particular, it is preferably in a liquid or a creamy form.

EXAMPLES

Having generally described this invention, a further understanding can be obtained by reference to certain specific examples which are provided herein for purposes of illustration only and are not intended to be limiting unless otherwise specified.

Example 1

Compositions were prepared using mixtures of the components shown in Table 1. The compositions were used to clean the inside portion of a human arm for one minute at 40° C. The conductance value of the skin was measured before cleaning and five minutes after cleaning. Table 1 indicates the relative conductance values, thus obtained with respect to the conductance value measured before cleaning, which is considered as a value of 100.

TABLE 1

| Component | Compa 1 | Compa 2 | Compa 3 | Compa 4 | Present 1 (%) |
|---|---|---|---|---|---|
| (1) Isostearic acid myristic acid glycerol diester | — | — | 2 | — | 2 |
| (2) Tri-2-ethyl-hexanoic acid glycerol ester | 2 | — | — | — | — |
| (3) Ethyleneglycol distearate | — | — | — | 2 | — |
| (4) Alkyl glucoside ($C_{12}H_{25}$—O—$(G)_{1.5}$, G: glucose) | 10 | 10 | 10 | 10 | 10 |
| (5) Polyoxyethylene-sec-tetradecyl ether (3.3EO) | 2.5 | 2.5 | 2.5 | 2.5 | 2.5 |
| (6) Glycerol | 10 | 10 | 0 | 10 | 10 |
| (7) Water | Ba | Ba | Ba | Ba | Ba |
| Conductance value (Relative value) [Before treated = 100] | 70 | 60 | 70 | 70 | 120 |

Compa: Comparative sample
Present: Present sample
Ba: balance

In Examples 2 to 6, detergent compositions were prepared in the same manner as Example 1.

Example 2 (face cleaner)

| | |
|---|---|
| Monolauryl phosphate·triethanol amine salt | 25 (%) |
| Lauric acid triethanol amine salt | 15 |
| Isostearic acid myristic acid glycerol ester | 3 |
| Glycerol | 10 |
| Dibutylhydroxytoluene | 0.3 |
| Perfume | 0.5 |
| Purified water | balance |
| | 100.0 |

Example 3 (Body shampoo)

| | |
|---|---|
| Sodium polyoxyethylenelauryl ether sulfonate (2 to 3EO) | 30 (%) |
| Dioleic glycerate | 10 |
| Glycerol | 15 |
| Dibutylhydroxytoluene | 0.3 |
| Perfume | 0.5 |
| Purified water | balance |
| | 100 |

Example 4 (Face cleaner)

| | |
|---|---|
| Monolauryl phosphate·triethanolamine salt | 20 (%) |
| Di-(2-ethylenehexanoic acid) glycerol ester | 20 |
| Ethylene glycol | 10 |
| Sorbitol | 10 |
| γ-Tocopherol | 0.3 |
| Methylparaben | 0.5 |
| Perfume | 0.5 |
| Purified water | balance |
| | 100.0 |

Example 5 (Body shampoo)

| | |
|---|---|
| Alkyl glucoside ($C_{12}H_{25}$—O—$(G)_{1.3}$, G: glucose) | 10 (%) |
| Sodium polyoxyethelenelauryl ether sulfonate (3EO) | 10 |
| dioctanoic acid glycerol ester | 0.8 |
| Glycerol | 10 |
| Dibutylhydroxytoluene | 0.3 |
| Perfume | 0.5 |
| Methylparaben | 0.3 |
| Purified water | balance |
| | 100.0 |

Example 6 (Body shampoo)

| | |
|---|---|
| Lauric acid triethanolamine salt | 5(%) |
| Alkyl glucoside ($C_{10}H_{21}$—O—$(G)_2$, G:glucose) | 10 |
| 2-Ethylhexyl octyl glyceryl ether | 5 |
| Propylene glycol | 20 |
| γ-Tocopherol | 0.3 |
| Methylparaben | 0.3 |
| Perfume | 0.6 |
| Purified water | balance |
| | 100.0 |

What is claimed is:

1. A detergent composition comprising:
   (A) a glycerol derivative having the following formula (I)

$$R^1—X—CH_2—CH—CH_2 \atop \quad\quad\quad\quad\quad\quad |\quad\quad |\atop \quad\quad\quad\quad\quad\quad Z^1\quad Z^2 \quad (I)$$

wherein one of $Z^1$ and $Z^2$ represents $R^2$—Y— and the other of $Z^1$ and $Z^2$ represents —OH and wherein $R^1$ and $R^2$, which may be the same or different, represent hydrocarbon groups having a total carbon atom number of 13 to 40 and X and Y represent an oxygen atom or $$—CO—;\atop \|\atop O$$

(B) a water soluble polyhydric alcohol; and
   (C) a skin detergent effective amount of at least one amphoteric surfactant, wherein component (A) and component (C) are present in a ratio of from 1:1 to 1:100, by weight.

2. The detergent composition of claim 1, wherein component (A) is a liquid at 20° C.

3. The detergent composition of claim 1, wherein component (A) is 1,3-dialkyl glyceryl ether represented by the following formula (II):

$$R^1—O—CH_2—CH—CH_2 \atop \quad\quad\quad\quad\quad |\quad\quad |\atop \quad\quad\quad\quad\quad OH\quad OR^2 \quad (II)$$

wherein $R^1$ and $R^2$ are as defined above.

4. The detergent composition of claim 1, wherein component (A) is a diacyl glycerol.

5. The detergent composition of claim 1, wherein the content of component (A) is from 0.1 to 20% by weight, based on the total amount of detergent composition.

6. The detergent composition of claim 1, wherein component (B) is selected from the group consisting of diethylene glycol, ethylene glycol, dipropylene glycol, propylene glycol, butylene glycol, glycerol, diglycerol and sorbitol.

7. The detergent composition of claim 1, wherein the content of component (B) is from 1 to 90% by weight, based on the total amount of detergent composition.

8. The detergent composition of claim 1, wherein the content of component (C) is approximately 2 to 60% by weight, based on the total amount of detergent composition.

9. The detergent composition of claim 1, wherein component (A) is selected from the group consisting of 1,2-dialkylglycerol ethers, 1,3-dialkylglycerol ethers, 1,2-diacylglycerol and 1,3-diacylglycerol.

10. The cleaning agent composition of claim 8, wherein component (A) is a 1,3-dialkylglyceryl ether represented by the following formula (III)

$$R^1—O—CH—CH_2 \atop \quad\quad\quad\quad |\quad\quad |\atop \quad\quad\quad\quad OH^1\quad OR^2 \quad (III)$$

wherein $R^1$ and $R^2$, which may be the same or different, each represent hydrocarbon groups having a total carbon atom number of 13 to 40.

11. The detergent composition of claim 1, wherein component (C) is present in an amount greater than 10% by weight.

* * * * *

UNITED STATES PATENT AND TRADEMARK OFFICE
CERTIFICATE OF CORRECTION

PATENT NO.   :   5,856,284
DATED:       :   January 5, 1999
INVENTOR(S)  :   Hirokazu HAMADA et al It is certified that error appears in the above-identified patent and that said Letters patent is hereby corrected as shown below:

Column 6,    line 18, after "surfactant," should read --selected from the group consisting of imadazolium betaine, carbobetaine and sulfobetaine--.

Signed and Sealed this

Twenty-eighth Day of September, 1999

Attest:

Q. TODD DICKINSON

Attesting Officer            Acting Commissioner of Patents and Trademarks